United States Patent [19]
Clarke et al.

[11] Patent Number: 6,008,009
[45] Date of Patent: Dec. 28, 1999

[54] CENTRIFUGE-OPERATED SPECIMEN STAINING METHOD AND APPARATUS

[75] Inventors: Mark S. F. Clarke, League City; Daniel L. Feeback, Houston, both of Tex.

[73] Assignee: Universities Space Research Association, Columbia, Md.

[21] Appl. No.: 09/174,380

[22] Filed: Oct. 15, 1998

Related U.S. Application Data

[60] Provisional application No. 60/082,217, Apr. 17, 1998.

[51] Int. Cl.[6] .............................. C12Q 1/00; C12Q 1/08
[52] U.S. Cl. ...................... 435/40.5; 435/283.1; 435/960; 435/4; 422/50; 57/76
[58] Field of Search ................ 435/40.5, 4, 283.1, 435/960; 422/50; 57/76

[56] References Cited

U.S. PATENT DOCUMENTS

| | | | |
|---|---|---|---|
| 4,069,968 | 1/1978 | Herman | 233/14 R |
| 4,268,393 | 5/1981 | Persidsky et al. | 210/516 |
| 4,285,464 | 8/1981 | Latham, Jr. | 233/26 |
| 4,612,873 | 9/1986 | Eberle | 118/52 |
| 5,260,032 | 11/1993 | Muller | 422/102 |
| 5,589,400 | 12/1996 | Hayes | 436/177 |

OTHER PUBLICATIONS

Molina et al; Applied & Environmental Microbiology; pp. 601–606; (Mar. 1990).

*Primary Examiner*—Louise N. Leary
*Attorney, Agent, or Firm*—John Gibson Semmes

[57] ABSTRACT

A method of staining preselected, mounted specimens of either biological or nonbiological material enclosed within a staining chamber where the liquid staining reagents are applied and removed from the staining chamber using hypergravity as the propelling force. In the preferred embodiment, a spacecraft-operated centrifuge and method of diagnosing biological specimens while in orbit, characterized by hermetically sealing a shell assembly. The assembly contains slide stain apparatus with computer control therefor, the operative effect of which is to overcome microgravity, for example on board an International Space Station.

10 Claims, 2 Drawing Sheets

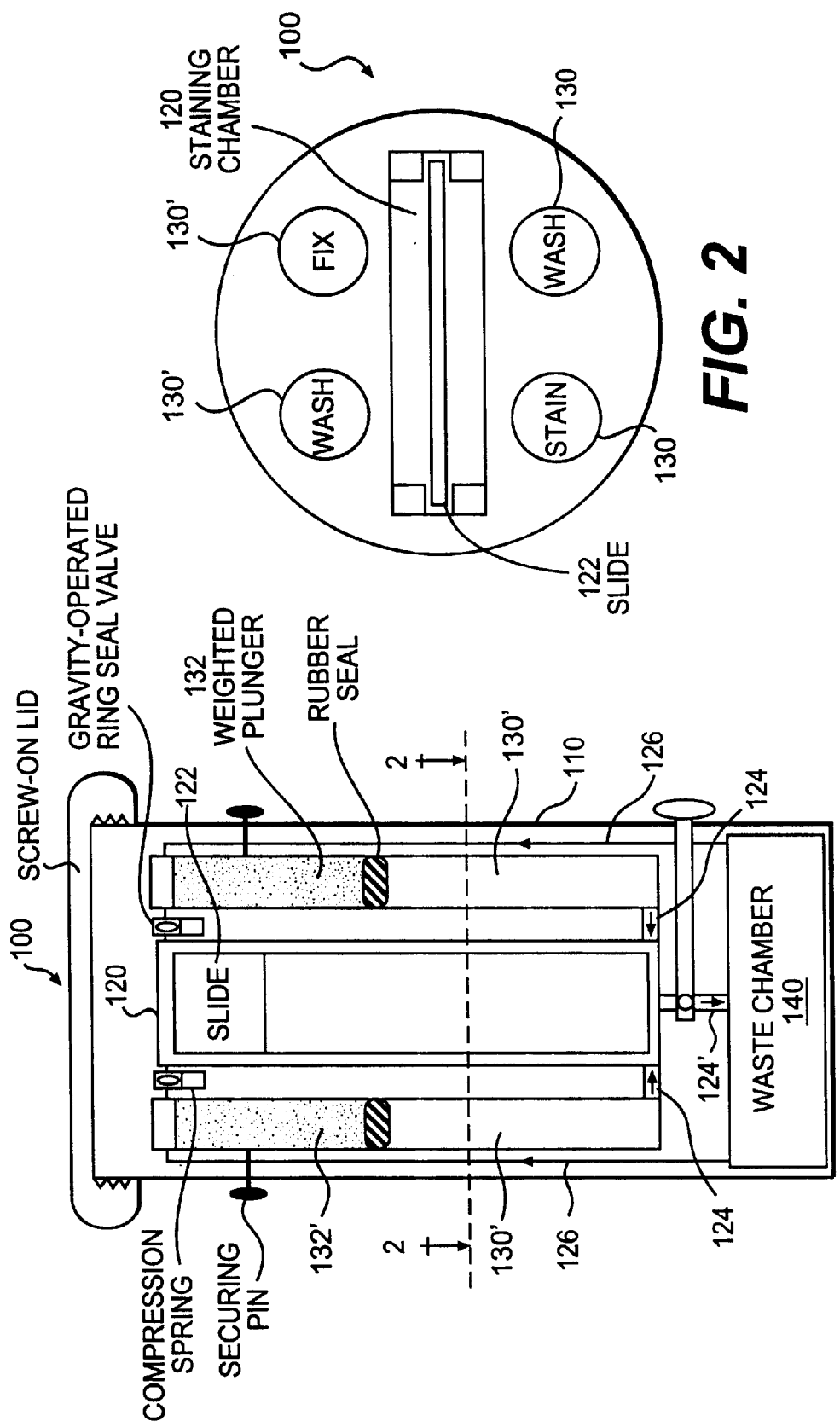

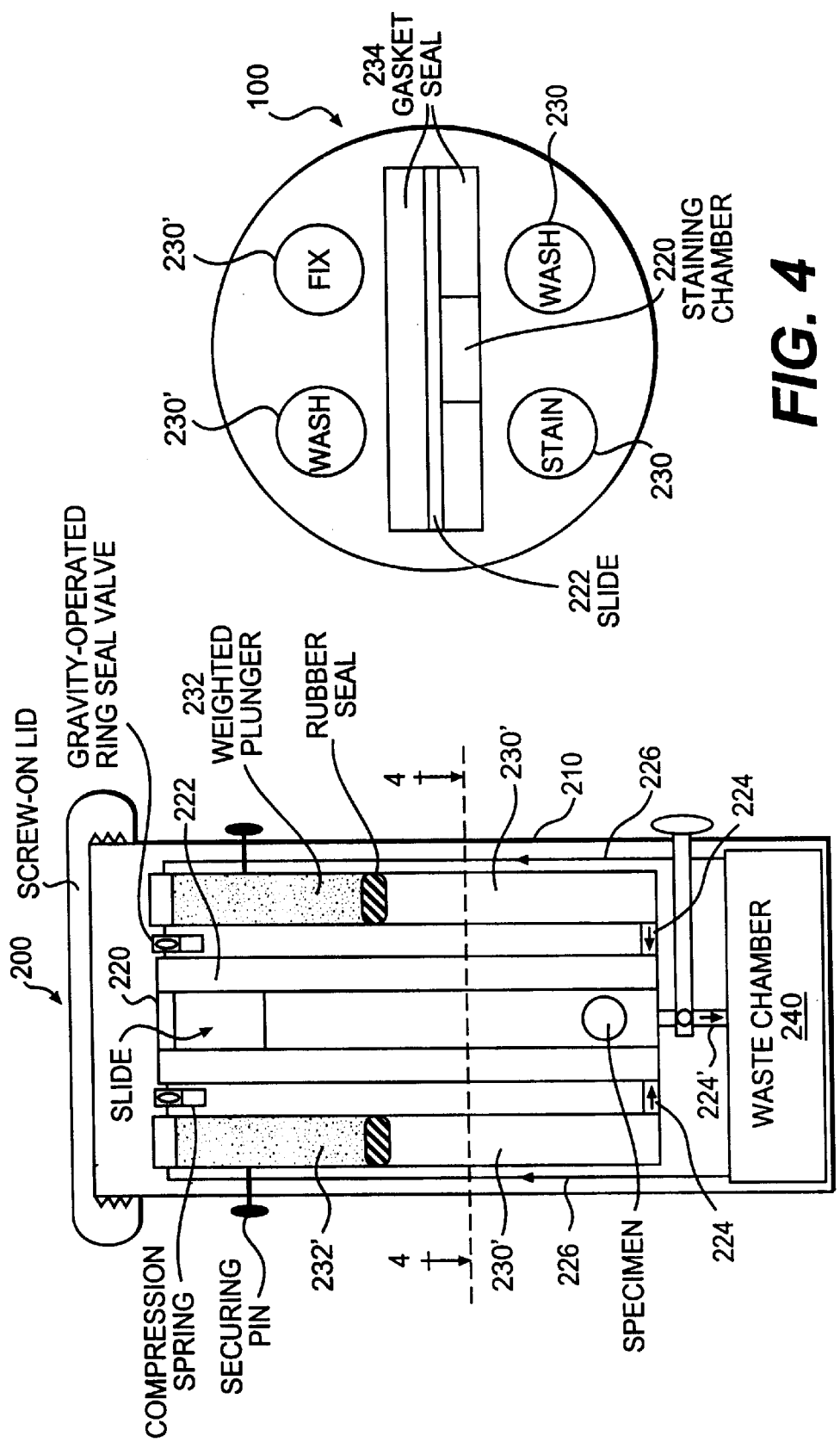

CENTRIFUGE-OPERATED SPECIMEN STAINING METHOD AND APPARATUS

RELATED APPLICATIONS

U.S. Provisional Application Ser. No. 60/082,217—filed Apr. 17, 1998 entitled Centrifuge-Operated Slide Staining Technology (COSST)

U.S. GOVERNMENT RIGHTS

This invention was made with Government support under contract NCC9-41 awarded by NASA. The Government has certain rights in this invention.

BACKGROUND OF INVENTION

A differential white cell count (DWCC) is an important diagnostic tool which can be used to distinguish between various conditions which induce alterations in the total number and type of white blood cells produced by the human body. For example, a DWCC can be used to distinguish between bacterial or viral infections, in the differential diagnosis of an allergic reaction or to detect the presence of myoproliferative disorders or leukemia on board an International Space Station, ISS.

Microgravity exposure during space flight results in hemodynamic changes in crew members, which in turn impacts upon the production of white blood cells. No data is presently available to establish the "normal baseline" for white blood cell production in microgravity. Without first knowing the extent to which microgravity exposure impacts white blood cell production, or secondly the proper "microgravity baseline" for a normal healthy crew-member in space, it is quite possible that a bacterial or viral infection may be overlooked or misdiagnosed, or that a potentially much more serious problem, such as leukemia, may be attributed to a bacterial or viral infection in a particular crew-member.

At the present time it is impossible to perform DWCC while aboard an orbiting space craft. Whole blood smears have been produced in microgravity, but as yet it has remained impossible to perform DWCC without returning the blood smear to Earth. Due to the limited life span of such smears it is impossible to make a definitive statement with regard to the effect of microgravity exposure upon white blood cell profile based on such samples. Until real-time performance and analysis of a DWCC can be achieved aboard the space craft, critical crew health information remains unobtainable.

In a terrestrial setting, a differential white cell count is obtained by firstly preparing a blood smear on a glass slide, fixing the cells in the smear to the surface of the slide, staining the cells with a histochemical stain followed by washing the slide in a clean buffer solution prior to viewing under the microscope where a differential white blood cell count is made by morphological criteria. The protocol outlined above is a simple and universally used technique to perform a DWCC. However, this technique requires the use of liquid buffer solutions, including fixatives and dye solutions. While this technique is performed easily on Earth, the problems associated with liquid handling in microgravity make such a task practically impossible.

Past attempts at solving this problem have induded several cell stainers which were tested by NASA or its contractor personnel but have since proved unsuitable for use in microgravity. The first attempt was a slide stainer which flew aboard Sky Lab. This device proved very cumbersome, required large volumes of buffer solutions and had limited use due to precipitate formation in the staining solutions which blocked the intricate tubing arrangement required to apply the staining solutions to the blood smear. A second attempt was based upon an airtight chamber design which contained a blood smear slide, into which buffer solutions and/or staining solutions were introduced using a vacuum system. System operation relied upon a series of one-way and two-way valves in order to achieve an efficient vacuum into which the staining solutions were introduced by hypodermic syringe. The original technology used a hand-held squeeze bulb to create the vacuum which proved inadequate. A later version incorporated mechanical pumps to provide both vacuum production and syringe emptying. The hand-operated version of this technology, although shown to work on the ground and which passed initial testing aboard the KC-135 parabolic aircraft, did not fulfill its potential; thus this technology has been shelved as a viable solution to slide staining on-orbit, not least because of its requirement for substantial crew interaction.

PRIOR ART

| INVENTOR | DATE | PAT. NO. | DESCRIPTION |
| --- | --- | --- | --- |
| Herman. | 1978 | 4,069,968 | Disposable Tubing Harness |
| Persidsky et al. | 1981 | 4,268,393 | Apparatus for Centrifugal Separation |
| Latham, Jr. | 1981 | 4,285,464 | Apparatus for Separation of Blood |
| Eberle | 1986 | 4,612,873 | Centrifuge Chamber |
| Muller | 1993 | 5,260,032 | Integral Centrifuge Tube |
| Hayes | 1996 | 5,589,400 | Distributing Material onto a Microscope |

SUMMARY OF INVENTION

The term "slide" as used herein encompasses employment of a standard glass or plastic microscope specimen slide or a filter whereby biological cells contained in a blood sample or tissue culture medium sample can be separated from the fluid portion of the sample. Specimens, trapped on or in such a filter, may be stained as herein defined, the filter being configured in the form of a standard specimen slide.

In microgravity, one of the major cohesive forces responsible for the physical properties of a liquid on earth, namely surface tension, is reduced. In addition, by definition an object, including a liquid, continues to have mass but not weight in zero gravity. As a consequence, liquids behave differently in microgravity than in normal gravity. One specific example of reducing the surface tension of a liquid in microgravity is that if a volume of liquid is introduced into a confined volume of space, such as a test-tube, it will form much larger droplets than it does in terrestrial gravity. In combination with this effect and the lack of weight the liquid exhibits in microgravity, the liquid will not form a discrete column of liquid in the bottom of the test-tube as it would on Earth, but rather a mixture of air and water dispersed throughout the volume of the test-tube. This has, and continues to be, a recurring problem with regard to liquid handling in microgravity. Staining of biological specimens on Earth is achieved by placing the specimen in containers full of liquid staining solutions. Due to the problems associated with liquid handling in microgravity this approach to staining biological specimens in space has to date met with little success. The invention described herein thus achieves staining of slide-mounted specimens using liquid reagents during space flight by removing the source of the problems associated with liquid handling in space, namely microgravity. This is achieved by incorporating a device which operates inside the standard laboratory centrifuge, manifested for flight on the International Space Station. This device, termed the Centrifuge-Operated Slide Staining or COSS unit, operates inside the on-board spinning centrifuge, thus negating any problems associated with liquid handling due to lack of gravity. The COSS unit operates within a sealed shell. All buffers/staining solutions are contained in disposable cartridges which are sequentially emptied by the centrifugal force produced within the spinning centrifuge when a retaining pin is removed from the weighted plunger assembly. Air displaced from the staining chamber is vented to the space previously occupied by the cartridge plunger. Staining solution or buffer is expelled from the staining chamber by activation of a one-way valve at the base of the staining chamber into a disposable waste container situated at the base of the COSS unit. Again, displaced air is vented back to the staining chamber. The one-way valve to the waste chamber is then closed and the staining chamber is then again filled with the appropriate buffer/staining solution. Air venting during operation of the COSS unit within the centrifuge is achieved by a gravity-operated ring seal valve which is open at more than 1×g but closes upon return to microgravity after the centrifuge stops spinning.

DESCRIPTION OF THE DRAWINGS

In each of FIGS. 1 and 3 the symbol Z,1 represents liquid movement during centrifugation; the symbol Z,2 represents displaced air movement during centrifugation.

FIG. 1 is a schematic view in vertical section of one form of COSS apparatus herein.

FIG. 2 is a schematic view in horizontal section of the present COSS apparatus taken along the line 2—2 of FIG. 1.

FIG. 3 is a schematic view in vertical section of a second embodiment of the COSS apparatus.

FIG. 4 is a schematic view in horizontal section of the COSS apparatus of FIG. 3 along the line 3—3 thereof.

DESCRIPTION OF PREFERRED EMBODIMENTS

The COSS apparatus has been created primarily to solve a problem raised by the requirement for real-time analysis of crew-member blood samples, specifically the requirement for a DWCC, preparation of which, on-orbit at the present time, is impossible. The device 100 is thus the first slide staining device designed to operate with a centrifuge to overcome the problems of liquid handling in microgravity. The hermetically sealable shell assembly 110 is simple and easy to use with minimal crew-member training required. The final device is fabricated so that it operates without the need for crew-member supervision, except for placing the blood smear slide into its staining chamber 120, sealing the device, placing it into a sealed on-board centrifuge, not shown, and switching on the centrifuge. The device will control buffer/staining solution entry to the staining chamber and evacuation of the solutions to the waste chamber 140 via an integral microprocessor chip, secured in the lid. This microprocessor will be programmed to apply and remove staining solutions or buffers to blood smear slide 122 after requisite fixing, staining or washing times by allowing disposable cartridge plungers 132–132', releasable by electromechanical means, to descend sequentially, thereby forcing a buffer solution up into the staining chamber 120. After the requisite interval, staining chamber 120 is evacuated between applications of required buffer solution by opening of one-way valve 124' to the waste chamber 140. As the COSS device will operate only in the greater than 1×g environment produced within the on-board centrifuge, liquid movement will always be in the direction of the gravity vector, i.e. towards the base/waste chamber 140 of the device. This method and apparatus completely abolishes the problems associated with liquid handling in microgravity, such as mixing problems, air bubbles remaining in the liquid resulting in improper staining, air bubbles becoming trapped in tubing or corners of the staining chamber 120 i.e. which prevents access and flow of the liquid to the blood smear slide 122 and removal of the liquid once it has performed its requisite task. In addition, since the present device operates as a sealed unit, the risk of escape of staining solutions into the crew compartment is minimal, excepting catastrophic failure of both the present device and the sealed chamber of the centrifuge.

The COSS device 100 functions using pairs of disposable cartridges 130–130' which contain the fixing, staining and wash buffer solutions required for a DWCC and a disposable waste container 140 to store the used staining buffers. See FIG. 2. In this configuration, the present device will be essentially reusable except for the disposable elements thereof, namely the buffer cartridges 130–130'slide 120 and waste container 140. Due to the use of a hypergravity environment, the volumes of buffer and staining solutions can be kept to a minimum as the solutions will be applied to the slide 120 as an intact sheet of liquid with no air bubbles. This is ensured due to rising of the liquid level in the staining chamber 120 as it is expelled from individual cartridges 130–130' by respective weighted plunger arms 132–132' of the cartridges 130, without mixing with the air in the chamber 110. That air is, in turn, vented back via conduits 126 to the space previously occupied by respective cartridge plungers 132 through the gravity operated ring seal valves 124.

This specific apparatus is important not only for minimizing waste material aboard the spacecraft, but also for potential commercial applications in a terrestrial setting. These include "hand-free" preparation of DWCC blood smears by non-technical personnel at remote medical facilities or use of the technology for adaptations such as in situ hybridization protocols carried out on tissue sections/isolated cell preparations in which extremely small volumes of liquid reagents are preferred or obligatory due to the large expense or scarcity, respectively, of the reagents. A preferred second embodiment of the COSS device for such an adaptation is illustrated in FIGS. 3 and 4 in which the slide 222 forms one wall of the staining chamber 210. Liquid reagent volume can be reduced to a minimum by mounting the specimen at the base 224 of the slide 222 and minimizing the thickness of the gasket seal 234. Conduit 226 vents air to the plunger space. Theoretically, a 10 mm square by 10 microns thick biological specimen, such as a frozen tissue section, mounted on a standard slide placed into the COSS device illustrated in FIG. 3, in which the dimensions of the staining chamber 220 are 20 mm wide 20 mm high and 20 microns thick, delineated by the dimensions of the gasket seal 234 and the volume of liquid introduced into the staining chamber in a hypergravity environment can be stained using a volume of liquid reagent of 7 microliters. In addition, as the reagents pass through one-way valve 224' and are collected into the waste chamber 240, after being applied to the specimen in the staining chamber 210, value reagent can be reclaimed if required. A third adaptation, in which the COSS technology proves useful, are those staining protocols which utilize immunoglobulin staining of tissue sections or single cells. These protocols, generically referred to as immunochemical staining protocols, usually require the permeabilization of the sample with detergent, application of multiple immunoglobulin reagents at specific concentrations for particular periods of time, interspaced with buffer washes and are very sensitive to the sample "drying out". The ability of the COSS technology to be "pre-programmed" with all of the above experimental parameters and to avoid any "drying out" of the sample ensures a highly reproducible, controllable, automated and hence error-free staining method. The present COSS technology thus lends itself to using extremely small volumes of reagents due to the behavior of liquid at higher than 1×g vectors. By design, the liquid "stays together as a column or sheet in an enclosed space such as the staining chamber 120 of the COSS device, per se."

One other configuration of the COSS device comprises a completely disposable unit except for the reusable microprocessor control elements contained in the lid of the device. This configuration is employed primarily to reduce crew member interaction, such as reloading of disposable cartridges. However, due to the envisaged long-term presence aboard the ISS, disposable cartridge systems are the preferred configuration.

The COSS device may also be produced so that it may contain multiple cartridges containing reagents for staining protocols which may be of use in other areas of spacecraft operation. These include a gram stain or calcofluor white stain for monitoring bacterial or fungal contamination respectively of the on-board water or air supply. In addition, biospecimens collected from crew members, including blood or urine smears, can be stained for the presence of micro-organisms or clinically important cell types utilizing a variety of different histochemical or immunochemical staining protocols. Furthermore, tissue sections from experimental plants or animals harvested on board the space craft, or isolated cells derived from prokaryotic or eukaryotic tissue cultures grown aboard the space craft can also be stained in a similar fashion for a variety of important biological molecules. The COSS device is not limited to staining only specimen slides but may also be used to stain filters, configured in the shape of a slide, on which single cells have been trapped or separated from liquid samples.

The present invention, described in detail in the foregoing preferred embodiments and demonstrated in its examples thereof, is subject to alterations and modifications by those skilled in the art. For example, the method and apparatus may employ up to thirty cartridges, each containing a different liquid reagent, depending upon the staining protocol desired. Such alterations and modifications, inherent in the invention, are encompassed within the scope of the invention as claimed.

We claim:

1. A protocol for staining at least one mounted specimen of either biological or non-biological substances using comparatively small volumes of liquid staining reagents:
    a) physically confining the specimen in a small space defined as an air containing staining chamber;
    b) forcing at least one liquid staining reagent into an air displaceable staining chamber from the base of said chamber;
    c) sequentially introducing at least one liquid staining reagent into said air displaceable staining chamber under hypergravity conditions produced within an operating centrifuge, whereby the hypergravity conditions maintain a highly discrete interface between liquid and gaseous phases of the specimen within said staining chamber by increasing both the relative weight and surface tension of the liquid staining solution, thereby to prevent mixing of said liquid staining reagents with air as they enter the staining chamber and to vent air therein.

2. The protocol of claim 1 wherein the minute volumes of differing liquid staining reagents are releaseably contained in plural cartridges, not to exceed thirty in number.

3. The protocol of claim 2 wherein the specimen is mounted on a standard biological slide prior to introduction in the staining chamber.

4. The protocol of either claim 3 wherein the specimen is mounted on a filter, configured as a standard biological specimen slide, prior to introduction of the specimen into the staining chamber.

5. The protocol of claim 3 wherein the surface of the standard biological slide on which the specimen is mounted defines in part, one side of the staining chamber.

6. The protocol of claim 4 wherein the surface of the standard biological slide on which the specimen is mounted defines in part, one side of the staining chamber.

7. A protocol for staining preselected, mounted specimens of either biological or non-biological substance in a terrestrial or extraterrestrial environmental including:
    a) confining the specimens to be stained;
    b) preventing air/liquid staining solution mixing within a staining chamber by conducting the staining in a hypergravity environment created within a standard centrifuge;
    c) concurrently introducing to a given specimen volume, at least one comparatively minute volume of a liquid reagent.

8. The protocol of claim 7 wherein the minute volumes of differing liquid reagents are releaseably contained in plural cartridges, not to exceed thirty in number.

9. The protocol of claim 8 wherein confining the specimens is by means of a standard biological specimen slide.

10. The protocol of claim 9 wherein confining of the specimen is by filter means, configured substantially in dimensions of a standard biological specimen slide.

* * * * *